United States Patent [19]
Watson

[11] Patent Number: 5,743,732
[45] Date of Patent: Apr. 28, 1998

[54] WOVSANIKER DYNAMIC JAW MODEL

[76] Inventor: Jeffrey A. Watson, 5023 Pine Valley Dr., Fayetteville, N.Y. 13066

[21] Appl. No.: 722,897

[22] Filed: Sep. 27, 1996

[51] Int. Cl.⁶ ...................................................... A61C 19/04
[52] U.S. Cl. .................................. 433/55; 433/56; 433/69
[58] Field of Search ............................ 433/52, 53, 54, 433/55, 56, 57, 58, 63, 68, 69, 72

[56] References Cited

U.S. PATENT DOCUMENTS

| | | | |
|---|---|---|---|
| 1,180,745 | 4/1916 | Lipp . | |
| 1,322,387 | 11/1919 | Wilson . | |
| 1,324,429 | 12/1919 | Mannon . | |
| 1,488,335 | 3/1924 | Gambill . | |
| 1,635,766 | 7/1927 | Priest . | |
| 1,661,119 | 2/1928 | Gambill . | |
| 2,258,471 | 10/1941 | Scott . | |
| 3,239,935 | 3/1966 | Shackelford | 433/69 |
| 3,349,489 | 10/1967 | Shackelford | 433/68 |
| 3,390,459 | 7/1968 | Seidenberg | 433/69 |
| 4,265,620 | 5/1981 | Moro et al. | 433/69 |
| 4,330,276 | 5/1982 | Becker et al. | 433/69 |
| 4,417,873 | 11/1983 | Kulas | 433/57 |
| 4,468,198 | 8/1984 | Kataoka et al. | 433/63 |
| 5,006,065 | 4/1991 | Waysenson | 433/63 |
| 5,055,041 | 10/1991 | Eckland | 433/56 |
| 5,366,373 | 11/1994 | Mumolo et al. | 433/58 |

FOREIGN PATENT DOCUMENTS

| | | | |
|---|---|---|---|
| 878276 | 11/1981 | U.S.S.R. | 433/54 |
| 9519151 | 7/1995 | WIPO . | |

*Primary Examiner*—Ralph Lewis
*Attorney, Agent, or Firm*—Trapani & Molldrem

[57] ABSTRACT

The present invention is concerned with apparatus and methods in the field of dentistry and in the field of design and testing of dental fixtures, components and materials. The apparatus comprises a jaw model having a mandible and a maxilla; a loading mechanism, coupled to the jaw model, for imposing an occlusal force on the mandible and maxilla; a mechanism(s), coupled to the mandible of the jaw model, for moving the mandible relative to the maxilla; and a load or force sensing device for sensing occlusal forces on the mandible and the maxilla of the jaw model. The mandible is caused to move laterally and protrusively using electric motors. A strain gauge meter may be coupled to the load sensing device, for measuring and displaying the forces sensed by the sensing device. A digital processor may also be employed for storing and recording the forces measured by the meter.

33 Claims, 6 Drawing Sheets

WOVSANIKER DYNAMIC JAW MODEL

BACKGROUND OF THE INVENTION

1. Technical Field

The present invention relates generally to dentistry including prosthodontics, and more particularly to apparatus and methods for modelling the physiological dynamics of dentulous or edentulous jaws for the purposes of testing, demonstration and education.

2. Background Art

In dentistry, there has been a need for educational tools and models for demonstrating to students of dentistry and other related professions how the human jaw operates. In addition, such tools and models have been necessary for informing patients about dental procedures being proposed as treatment. In many cases, such devices are very effective in conveying the information needed by the patient to give his or her informed consent.

To this end, various devices have been developed to model the human jaws with teeth (i.e., dentulous) for educational and demonstrative purposes. For example, Columbia Dentoforms, New York, N.Y., has developed a product called the "Typodont" which is a working model of the maxilla and mandible, including temporomandibular joints, artificial gums and teeth. The Typodont has become a popular study tool in dental schools. Among other things, the Typodont permits the student to manually move the mandible relative to the maxilla, to study various mandibular movements and to understand occlusion.

While the Typodont and other similar devices have become very successful educational tools, there is still room for improvement and additional functionality. For instance, in these pre-existing devices, the mandibular movements are to be effected manually, and the user must be sure that the movements are physiologically accurate. As a result of manual operation, repeatability of particular movements becomes difficult. Furthermore, such devices do not model other physiological aspects of the jaws, for example, stresses on the maxillary and mandibular teeth during static occlusion, or dynamic activity such as chewing or grinding. The need, therefore, persists for a more versatile teaching and educational aid for students and patients.

In the past, efforts have been made to animate dental articulators for the purpose of fitting or grinding dentures and other prostheses. For example, U.S. Pat. No. 5,006,065 to Waysenson, U.S. Pat. No. 4,330,276 to Becker et al., U.S. Pat. No. 2,258,473 to Scott, U.S. Pat. No. 1,635,766 to Priest, and U.S. Pat. No. 1,488,335 to Gambill, all disclose dental articulators using motors to move one dental model or cast relative to another, in an articulator structure. The aforementioned patents to Scott and Gambill also disclose the use of an elastic band or spring for exerting occlusal pressure between the upper and lower dental models for grinding dentures or other prostheses. While these devices may have found some utility in fitting or grinding dentures, they are limited as an educational or demonstrative tool, or as a device for testing dental components. They lack means for sensing the occlusal forces on the dental models or casts, or a convenient means for adjusting such forces. Further, such articulator devices do not offer a realistic jaw model which is constructed to receive various dental components for test and demonstration purposes. It is perhaps because of these limitations that such articulators have not been seriously considered as an educational tool or as a testing platform. A survey of the industry, conducted by the inventor herein, has not uncovered any of the above-mentioned articulators in use.

An articulator device has been proposed in U.S. Pat. No. 5,055,041 to Eckland, for measuring the pressure transmitted to the mandibular alveolar ridge of a lower denture. It is also suggested that the device be used to measure the pressure necessary to shear off various types of food specimens. However, the device in Eckland is limited as a testing device in that there is no mandibular movement during testing. Furthermore, the Eckland patent fails to suggest that such mandibular movement would be desirable for either educational or test purposes.

Also in the field of dental implant design and dentistry, there has been the need to test the strength, reliability, and durability of new dental implant designs and materials. Heretofore, such dental implant testing has been performed outside a realistically modelled operational environment. For example, such tests have merely involved basic load or impact testing of individual implant fixtures in standard engineering test jigs (i.e., in the category of the "drop test"). The need remains for more a realistic test procedure and an apparatus for carrying out such a procedure.

OBJECTS AND SUMMARY OF THE INVENTION

It is therefore an object of the present invention to provide apparatus and methods that avoid the aforementioned problems associated with the prior art.

It is another object of the present invention to provide an apparatus for modelling the physiological dynamics of a human or an animal jaw, including accurate mandibular movement and realistic occlusal forces.

It is a further object of the present invention to provide a realistic and dynamic jaw model as a study aid for students of dentistry, medicine and other related professions.

It is yet another object of the present invention to provide a realistic and dynamic jaw model particularly suited for educating patients about proposed dental treatments and procedures.

It is yet a further object of the present invention to provide methods and apparatus for testing and demonstrating the performance, reliability, strength, and durability of dental components and dental materials in a realistic, but simulated operational environment.

These and other objects are obtained in accordance with the present invention wherein there is provided, an apparatus for modelling the physiological dynamics of a jaw. The apparatus comprises a jaw model having a mandible and a maxilla; a loading mechanism, coupled to the jaw model, for imposing an occlusal force on the mandible and maxilla; a mechanism(s), coupled to the mandible of the jaw model, for moving the mandible relative to the maxilla; and a force sensing device for sensing occlusal forces on the mandible and maxilla.

The mechanisms for effecting movement of the mandible include electric motors and specifically designed mechanical drives coupled between the motors and the mandible. With such mechanisms, the mandible of the jaw model can be made to undertake either lateral or protrusive excursions, or both lateral and protrusive excursions.

The present invention may also include the use of a strain gauge meter, coupled to the load sensing device, for measuring the forces sensed by the sensing device. The strain gauge meter may include an LED display for displaying the measured forces. A computer or digital processor may also be employed for storing and recording the forces measured by the strain gauge meter. In addition, the computer or processor may be used to count and store the number of lateral and/or protrusive excursions (or cycles) undertaken by the mandible.

In the preferred embodiment, the loading mechanism includes a hollow plunger in telescoping relation to an adjustable loading member. A compression spring is seated inside of the plunger and the loading member. The compression spring produces a direct force and a reactive force when the spring is compressed. The reactive force is proportional to the direct force. The direct force is transmitted to the plunger and the reactive force is transmitted to the loading member. The plunger urges the mandible against the maxilla with the direct force to produce an occlusal force on the mandible and maxilla. The reactive force imposed on the load member is sensed by the sensing device. The sensing device may be, for example, a load cell. The amount of force applied to the mandible is adjustable by adjusting the loading member, or by replacing the compression spring with another spring that can deliver a greater or lesser amount of force after being compressed.

The mandible and maxilla of the jaw model each include a mounting plate to which dental fixtures, such as artificial teeth, may be secured. The mandible and maxilla may include a set of mandibular and maxillary teeth respectively. In addition, other types of dental fixtures may be secured to the mounting plates. For example, a complete dental implant restoration may be secured to the mounting plate of the mandible and/or maxilla. A complete implant restoration may be secured to one of the mounting plates by first securing a bushing in the plate, then threading an implant into the bushing, then threading an abutment into the implant, and then fastening an artificial tooth to the abutment with a screw.

A method of testing dental components and materials is also contemplated by the present invention. In the preferred embodiment, the method comprises the steps of: (1) fastening to a jaw model of the present invention a dental fixture (e.g., a complete dental implant restoration) with which the dental component (e.g., implant) or material under test is associated; (2) applying occlusal forces on the mandible and maxilla; (3) moving the mandible relative to the maxilla such that the dental component or material under test is stressed during such mandibular movement; and (4) sensing the forces on the mandible and maxilla of the jaw model during the mandibular movements.

The method of testing may further comprise the step of shaking the jaw model during the mandibular movements. Preferably, such movements include lateral and protrusive excursions of the mandible. The method may also include the step of adjusting the amount of occlusal force applied to the mandible and maxilla. The method may further include the steps of: measuring the forces sensed during the sensing step; displaying the forces measured during the measuring step; and recording the forces measured during the measuring step.

In the method of testing a dental implant, the jaw fastening step includes placing or inserting the dental implant under test into the model jaw (mandible or maxilla), and assembling a complete implant restoration, including an abutment and artificial tooth.

BRIEF DESCRIPTION OF THE DRAWING

Further objects of the present invention will become apparent from the following description of the preferred embodiments with reference to the accompanying drawing, in which.

DESCRIPTION OF THE PREFERRED EMBODIMENTS

Figure 1:
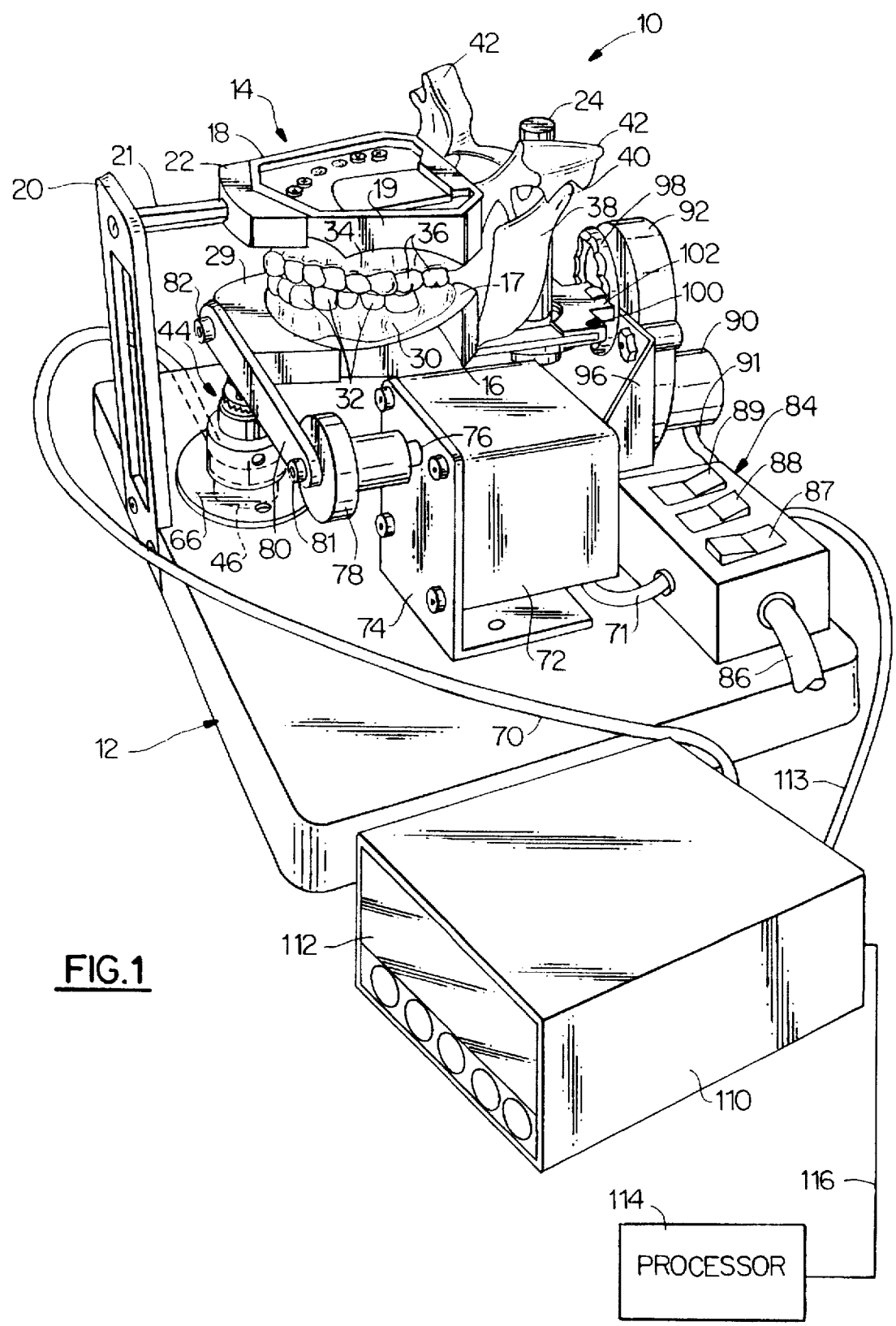
FIG. 1 is a perspective view of the dynamic jaw model apparatus of the present invention.
Figure 2:
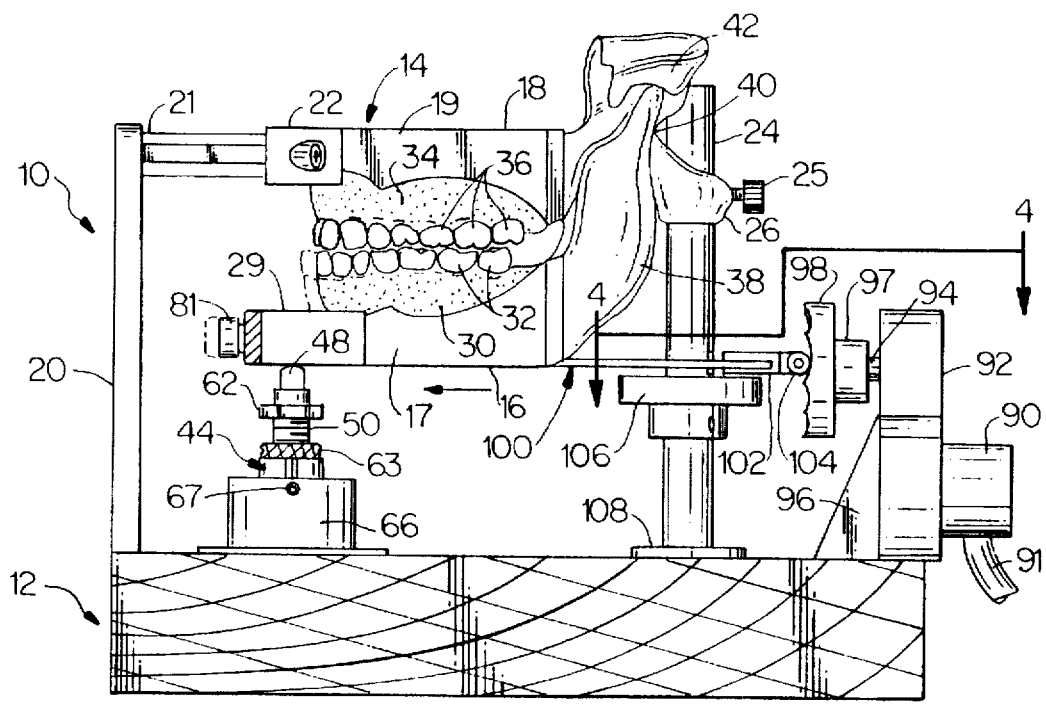
FIG. 2 is a partial section and side elevation view of the apparatus of FIG. 1, with certain parts removed to clearly illustrate the jaw model portion of the apparatus.
Figure 3:
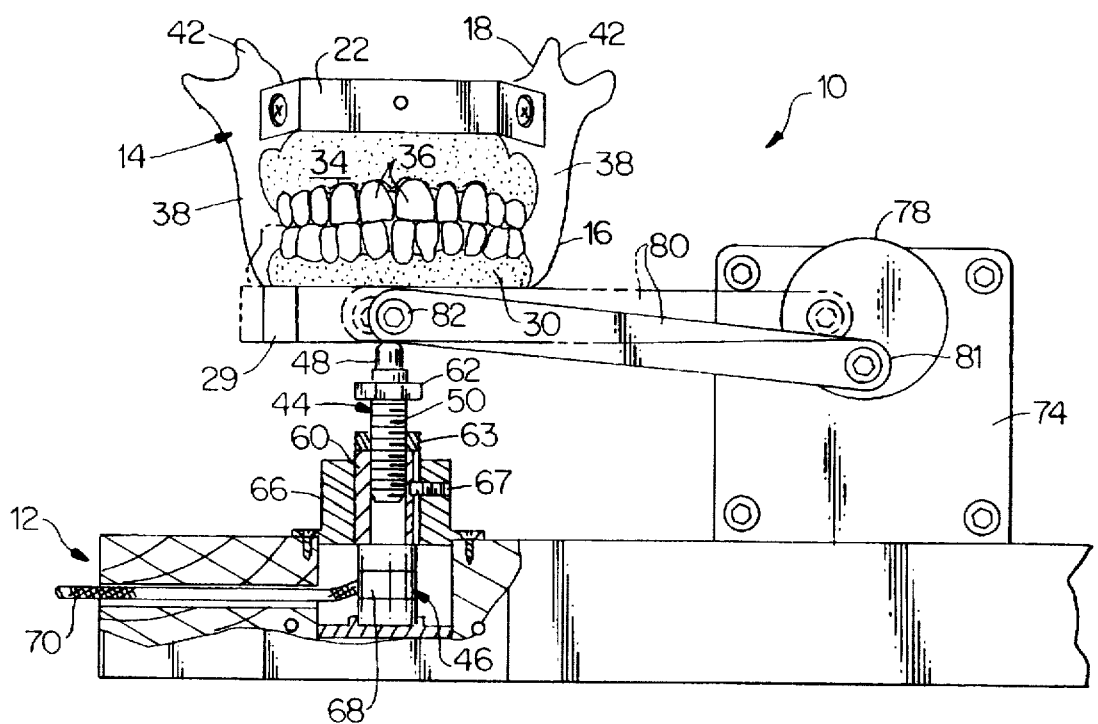
FIG. 3 is a partial section and front elevation view of the apparatus of FIG. 1, with certain parts removed and broken away to illustrate the loading mechanism and sensing device of the apparatus.

With reference to FIG. 1, there is shown a perspective view of a dynamic jaw model apparatus 10, constructed in accordance with the present invention. Apparatus 10 includes a base 12 upon which most of the components of apparatus 10 are mounted. Apparatus 10 further includes a jaw model 14 which has a dentulous (i.e., with teeth) mandible part 16 and a dentulous maxilla part 18. As shown in FIGS. 1 and 2, maxilla 18 is fixed in position by a bracket comprising an upright stanchion 20, a standoff 21, and mounting fixture 22. Stanchion 20 is securely mounted to base 12 by a pair of screws, and fixture 22 is securely mounted to maxilla part 18 by a pair of screws (FIGS. 2 and 3). Mandible part 16 is supported for lateral, occlusive, and protrusive movements as will be described hereinbelow.

Figure 9:
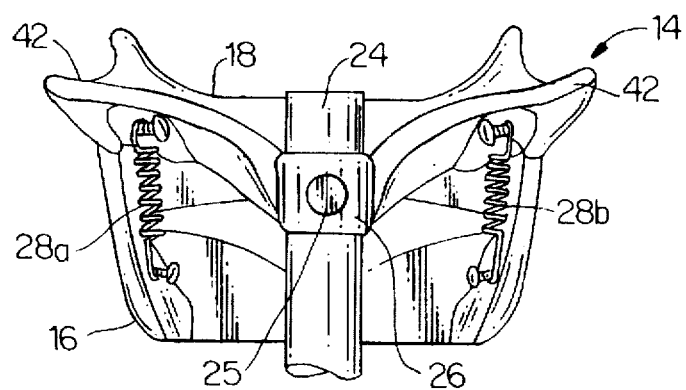
FIG. 9 is a rear elevation view of the jaw model portion of the apparatus of FIG. 1.

As best shown in FIGS. 2 and 9, maxilla part 18 is also adjustably clamped to an upright post 24 with a locking screw 25. Maxilla part 18 includes a rear extension 26 containing a bore through which post 24 passes (FIGS. 2 and 9). Locking screw 25 bears against post 24 to secure rear extension 26, and thus the rear portion of maxilla part 18.

As shown in FIGS. 1–3, mandible part 16 is supported to move laterally (side-to-side), occlusively (up and down), and protrusively (forward and back). As shown in FIG. 9, mandible part 16 is suspended from maxilla part 18 by a pair of tension springs 28a and 28b. Springs 28a and 28b allow mandible 16 to be displaced from a position of occlusion with maxilla 18. Springs 28a and 28b tend to bring mandible 16 back to a position of occlusion with maxilla 18 after a previously applied displacement force is removed from mandible 16. A mounting fixture 29 is fastened to the front portion of mandible 16; its function will be described hereinbelow.

With further reference to FIGS. 1–3, mandible part 16 includes artificial gums 30 and a set of artificial mandibular teeth 32. Maxilla part 18 also includes artificial gums 34 and a set of artificial maxillary teeth 36. Mandible part 16 further includes a ramus portion 38 on each side of mandible part 16. In addition, mandible part 16 includes a pair condyles 40, one on each side of mandible part 16. Maxilla part 18 includes a pair of glenoid fossae portions 42, which mate with condyles 40 to replicate a pair of temporomandibular joints.

The structure of jaw model 14, as described above, is commercially available as a single product supplied by Columbia Dentoforms, New York, New York, under the name, "Typodont," in the preferred embodiment, a Typodont is mounted to post 24 and to fixtures 22 and 29.

With further references to FIGS. 1–3 and 10, there is shown an adjustable loading mechanism 44 positioned below mandible 16, just under fixture 29 (FIG. 2). Loading mechanism 44 is intended to simulate the loads placed on the mandible and maxilla by the jaw muscles, including the masseter muscle. Loading mechanism 44 imposes an upward (or occlusal) force on mandible 16, which causes mandible 16 to be urged up against maxilla 18. It can be said that loading mechanism 44 urges mandible 16 into a position of occlusion with maxilla 18.

Figure 10:
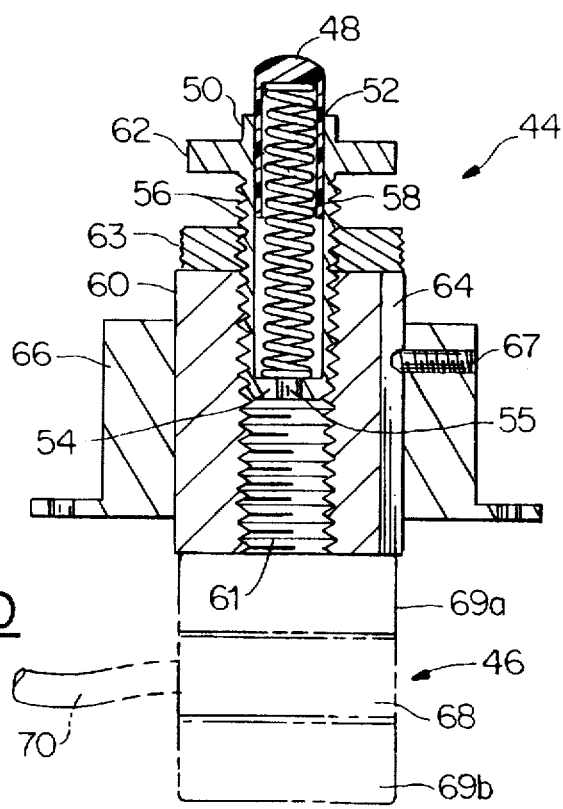
FIG. 10 is an enlarged view, showing the loading mechanism of the apparatus of FIG. 1 in section, and showing the sensing device of the apparatus of FIG. 1 in elevation.

As best shown in FIGS. 3 and 10, a sensor device 46 is positioned under loading mechanism 44, and functions to sense the occlusal force on mandible 16 and maxilla 18. As shown in FIG. 10, loading mechanism 44 includes a hollow plunger 48 in telescoping relation to a threaded loading member 50. Member 50 contains an open end 52 through which plunger 48 is received, and includes a substantially closed end 54 containing a small opening 55. Load member 50 further includes external threads 56. As shown in FIG. 10, a compression spring 58 is seated inside both plunger 48 and load member 50. Spring 58 produces both a direct force and a reactive force when it is compressed, in a well known manner. The reactive force is proportional to the direct force. As understood from FIG. 10, the direct force of spring 58 is transmitted to plunger 48 and the reactive force is transmitted to load member 50. By properly positioning load member 50 relative to mandible 16 (i.e., fixture 29), spring 58 causes plunger 48 to urge mandible 16 against maxilla 18 with the direct force.

As shown in FIG. 10, loading mechanism 44 also includes a bushing 60 containing a threaded bore 61. Load member 50 is threaded into bore 61, and can be adjusted up or down by turning member 50 clockwise and counter clockwise in bore 61. A hex flange 62, forming a part of load member 50, facilitates the turning of load member 50. Bushing 60 contains a grove 64 running lengthwise and along the outer peripheral surface of bushing 60 (FIG. 10). Bushing 60 passes through a collar 66, and is maintained in close sliding engagement with collar 66. As shown in FIG. 3, collar 66 is mounted to base 12 with a pair of screws. A set screw 67 is threaded radially through collar 66 and extends into grove 64. Set screw 67 prevents bushing 60 from rotating clockwise or counter clockwise inside collar 66.

As shown in FIGS. 3 and 10, bushing 60 rests on top of sensor device 46, and bears down on device 46 in response to the reactive force transmitted by compression spring 58 (i.e. the reactive force is transmitted to bushing 60 by way of load member 50). From this arrangement, the reactive force is sensed by device 46. A lock nut 63, having a knurled surface, is threaded on load member 50, and locks member 50 in place when threaded down against bushing 60.

Sensor device 46 is preferably a load cell device, such as the LCW Series Load Cell, supplied by OMEGA Engineering, Inc. of Stamford, Conn. In FIGS. 3 and 10, sensor device 46 is depicted as a load cell device, comprising a load cell element 68 and a pair of load buttons 69a and 69b. Buttons 69a and 69b are provided to ensure correct loading on load cell element 68. Load cell element 68 includes a cable 70 having two conductors for power and two conductors for an electric load signal generated by load cell 68. The load signal is proportional to the force applied to load cell element 68.

Referring back to FIGS. 1–3, there is shown a means for effecting lateral excursions of mandible 16. Such means comprises an AC motor 72 having a rated speed of about 10 revolutions per minute (RPM), at 60 Hz and 115 volts. Motor 72 is secured to a bracket 74 which, in turn, is mounted to base 12 by a pair of screws. Motor 72 includes a rotating shaft 76 which passes through a hole in bracket 74 (FIG. 1). A crank wheel 78 is secured to shaft 76 with a set screw, such that wheel 78 rotates with shaft 76. A crank arm 80 is rotatably coupled to wheel 78 by way of a screw passing through arm 80 and threaded into wheel 78. A greased cylindrical bushing (not shown) is inserted in a hole in arm 80, and acts as a bearing for the screw passing through arm 80. As best shown in FIG. 3, the connection of crank arm 80 to crank wheel 78 is at an eccentric point on wheel 78. Such an arrangement is necessary to convert the rotating motion of wheel 78 to a substantially linear motion of crank arm 80.

As shown in FIGS. 1 and 3, the other end of crank arm 80 is rotatably coupled to fixture 29 in the same way as described with respect to the coupling of arm 80 to crank wheel 78. As shown in FIG. 1, motor 72 is powered through a cable 71 which, in turn, originates from a junction switch box 84. Switch box 84 is powered by a cable 86 connected to a standard 120 volt, AC outlet. As shown in FIG. 1, switch box 84 has three switches 87, 88 and 89. When switch 87 is closed, it routs power from cable 86 to cable 71, thus powering motor 72. In operation, shaft 76 of motor 72 rotates, causing crank wheel 78 to rotate at about 10 RPM. Rotation of wheel 78 causes crank arm 80 to move laterally (left and right in FIG. 3) which, in turn, causes mandible 16 to move laterally. This movement is illustrated in FIG. 3 in phantom lines.

In accordance with the present invention, mandible 16006Xis also made to undergo protrusive excursions by employing a means best shown in FIGS. 1 and 2. The protrusive movement means comprises a small AC motor 90 having a rated speed of 2 RPM, at 115 volts and 60 Hz. Motor 90 is powered through a cable 91 which, in turns, originates inside switch box 84. Motor 90 is powered by closing switch 89. Once closed, switch 89 permits power to flow from cable 86 to cable 91. Motor 90 includes a rotating shaft (not shown) which is coupled to one end of a gear and bearing system contained in a gear box 92. A shaft 94 (FIGS. 2 and 4) is coupled to the opposite end of the gear and bearing system in gear box 92, and is made to rotate with the shaft of motor 90, by way of the gear and bearing system. The gears in gear box 92 transmit the 2 RPM speed of rotation of motor 90 to shaft 94. Gear box 92 and motor 90 are mounted to a bracket 96 by a pair of screws, and bracket 96 is mounted to base 12 by a pair of screws.

Figure 4:
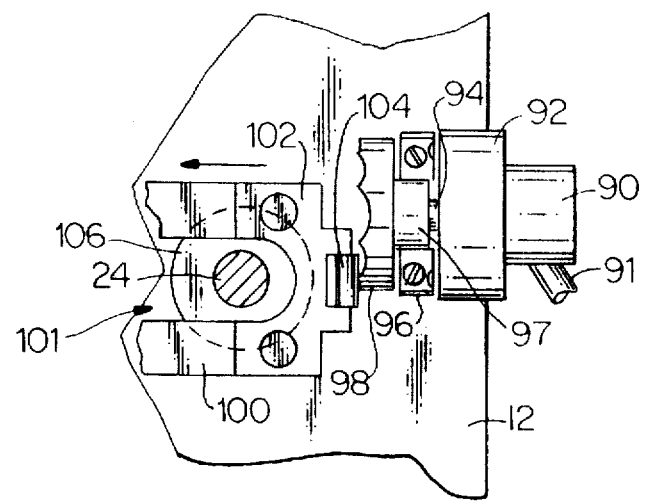
FIG. 4 is an enlarged fragmented view of the apparatus of FIG. 1, taken along line 4—4 in FIG. 2, showing the mechanism for effecting protrusive movement of the mandible portion of the apparatus.

As best shown in FIGS. 2 and 4, a cam wheel 98, having scalloped cam surfaces, is secured to shaft 94 at a hub 97. Cam wheel 98 is made to rotate with shaft 94. A linear drive arm 100 cooperates with cam wheel 98 at one end and is secured to mandible part 16 at its other end (FIG. 2). Drive arm 100 is constructed to form a slot 101 (FIG. 4) through which post 24 projects (See also FIG. 1). Slot 101 permits drive arm 100 to move forward and backward relative to post 24. As best shown in FIGS. 1 and 4, the cam wheel end of drive arm 100 includes a bilateral support 102 to which a cylindrical roller 104 is rotatably mounted. As best illustrated in FIGS. 2 and 4, roller 104 directly engages the cam surfaces of cam wheel 98, causing drive arm 100 to move in a reciprocating manner, forward and backward (left and right in FIG. 2). The action of drive arm 100 causes mandible part 16 to move through protrusive excursions, as indicated in phantom lines in FIG. 2. As shown in FIG. 2, bilateral support 102 is made to rest on and slide along a bearing flange 106. Bearing flange 106 is secured to post 24 by a set screw. Post 24 includes a base flange 108 for securing the post to base 12 with a pair of screws.

In FIG. 1, there is shown a strain gage meter 110 which receives load signals from load cell 68, by way of cable 70. As mentioned above, the load signals are proportional to the force imposed on load cell 68. Once meter 110 is calibrated, meter 110 will accurately measure the force placed on load cell 68. Meter 110 further includes an LED display 112 for displaying the force measurements made by meter 110. As shown in FIG. 1, meter 110 is powered by way of switch box 84 when switch 88 is closed. Meter 110 may be a commercially available strain gauge meter, such as the DP25-S OMEGA Strain Gage Meter, supplied by OMEGA Engineering, Inc., of Stamford, Conn. The OMEGA meter can be calibrated in units of Newtons, which is the preferred unit of measure.

Again referring to FIG. 1, there is shown a digital processor 114 connected to meter 110 by way of a data cable 116. In this embodiment, processor 114 is powered independently of apparatus 10. Processor 114 is employed for storing and recording the force measurements made by meter 110. Processor 114 may also be configured to control the operation of motor 72 and motor 90, and thus the movement of mandible 16. In addition, the number of excursions (or cycles of movement), both laterally and protrusively, could be counted and recorded by processor 114. Rotating shaft or linear motion encoders may be required to monitor speed and provide excursion (or cycle) count data to processor 114. Processor 114 may be configured to record the rate of motion, in numbers of excursions or cycles per minute. The rate of excursions, e.g., cycles per minute, may be controlled by processor 114 to accurately simulate the rates of human mandibular movements.

Attention is now directed back to jaw model 14. As shown in FIGS. 1-3, mandible part 16 includes a mounting plate 17, and maxilla part 18 includes a mounting plate 19. In the preferred embodiment, both mounting plates 17 and 19 are made of a hard plastic to enable one to drill into it for mounting artificial teeth, dental implants, and other dental fixtures. For the purpose of this application, the term "dental fixture" shall include: artificial teeth; dental implants; the entire implant structure including implant, abutment, and artificial tooth; attachment fixtures for dentures; and like devices.

Figure 5:
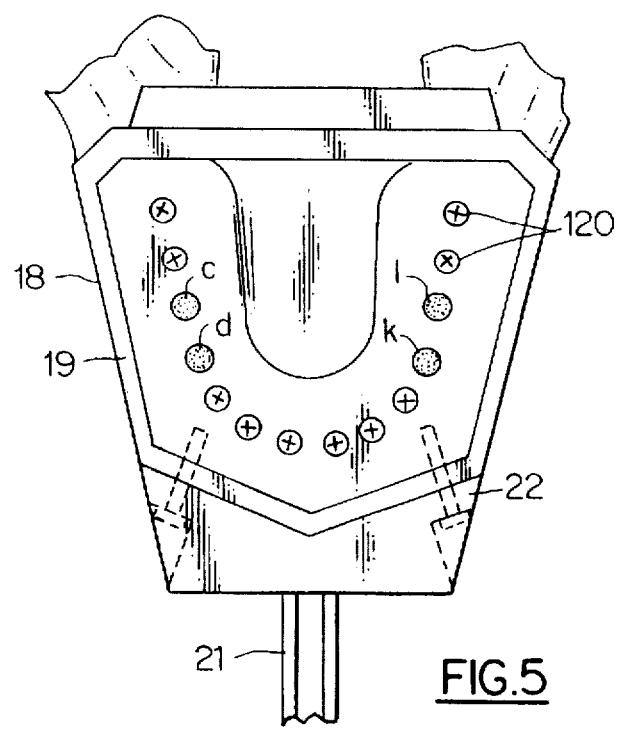
FIG. 5 is an enlarged fragmented view of the apparatus of FIG. 1, showing, from the top, looking down, the maxilla portion of the apparatus.
Figure 6:
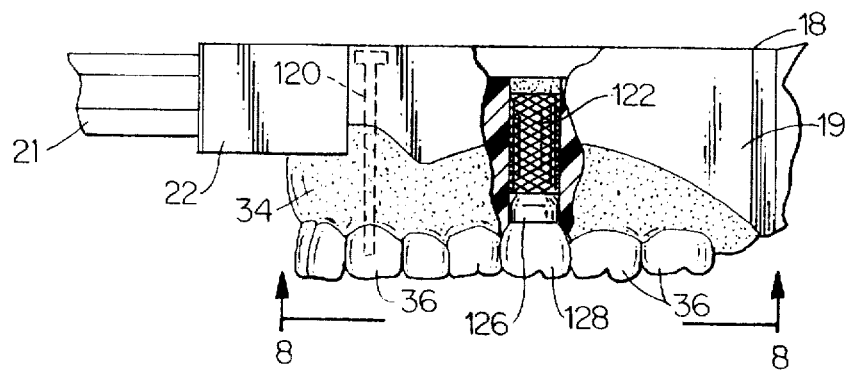
FIG. 6 is a side elevation view of the maxilla portion of the apparatus of FIG. 1, showing in section a complete dental implant restoration fastened to the maxilla portion.
Figure 8:
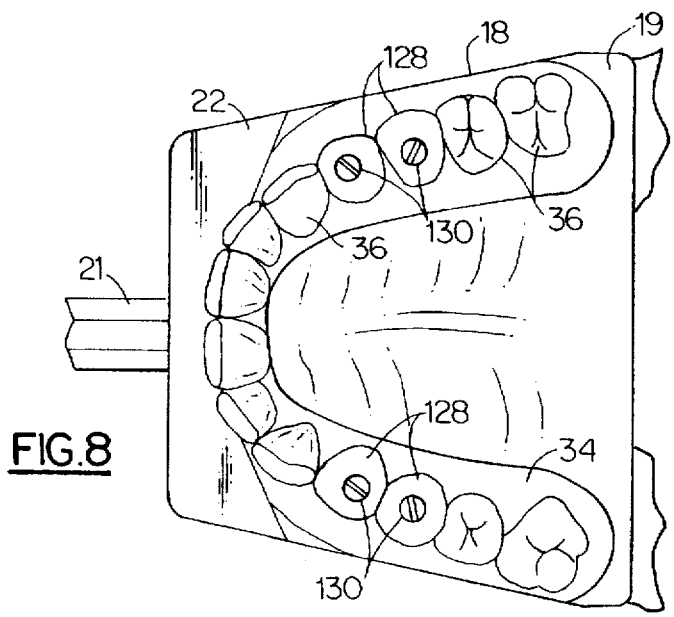
FIG. 8 is a bottom plan view, taken along line 8—8 in FIG. 6, showing the maxilla portion of the apparatus of FIG. 1.

As pointed out above, mandible 16 includes a set of artificial teeth 32, and maxilla 18 includes a set of artificial teeth 36. Each of the artificial teeth 32 and 36 are mounted to their respective mounting plates by way of mounting screws. FIG. 5 is a top plan view of mounting plate 19, showing a number of mounting screws 120. Each one of screws 120 secures an artificial tooth 36 to maxilla 18. FIG. 8 is a bottom plan view of maxilla 18 which shows artificial teeth 36 secured in place. FIG. 6 illustrates (in phantom lines) a screw 120 in place, securing artificial tooth 36. This method for mounting artificial teeth 32 and 36 is employed in the Typodont supplied by Columbia Dentoforms.

The placement (or insertion) of dental implants and related components in jaw model 14 will now be described with reference to FIGS. 5-8. This description will be primarily concerned with maxilla part 18; however, it is to be understood that the description is equally applicable to mandible part 16.

As indicated in FIG. 5, four mounting screws 120 have been removed at locations c, d, k and l, and the screw holes have been plugged up by a plastic cement or epoxy resin. The artificial teeth for locations c, d, k and l are removed with their respective screws. At each location c, d, k and l, a larger diameter bore is drilled into mounting plate 19, in the direction indicated by line 8-8 in FIG. 6. The diameter of the bore is made slightly larger than the outside diameter of a bushing 122 (See FIGS. 6 and 7). Bushing 122 is then inserted into the drilled out bore at each location c, d, k and l, and cemented into place using a plastic cement or epoxy resin. Bushing 122 is shown as having a knurled exterior surface which aids in bonding the bushing to mounting plate 19. Bushing 122 is intended to simulate the tapped or drilled hole made in the jaw bone in preparation for inserting a dental implant. Bushing 122 may be further reinforced by one or more set screws entering from the side of mounting plate 19. It is to be understood that bushing 122 may be installed at any mounting screw location around maxilla part 18 or mandible part 16.

Figure 7:
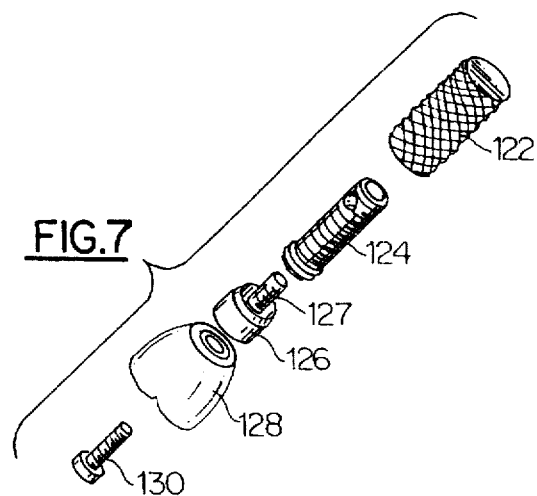
FIG. 7 is an exploded view of a complete dental implant restoration.

Once the epoxy resin or plastic cement has dried, an actual implant fixture 124 (FIG. 7) is tapped or threaded into bushing 122. To complete the implant restoration, an implant abutment 126 with a screw portion 127 is threaded into implant 124, and an artificial tooth 128 is fastened to abutment 126 with a screw 130 (FIGS. 7 and 8). Other forms of dental fixtures, as identified previously, can be installed on maxilla part 18 and/or mandible part 16.

A method of testing dental components and material will now be described. In the preferred embodiment of the method of the present invention, apparatus 10 is employed. Apparatus 10 is especially suited for testing dental components such as implant fixtures, implant abutments, artificial teeth, etc, and for testing dental materials such as alloys and composites. Due to accurate modelling of the structure and dynamics of the human jaws in apparatus 10, dental components and materials can be tested under a realistic operational environment. For example, dental prostheses intended to replace the two front upper teeth, can be tested at the two front upper teeth locations in jaw model 14. Similarly, prostheses intended for replacing molars or bicuspids can be tested in their proper locations in jaw model 14.

In accordance with the method of the present invention, a particular dental component or material to be tested is placed in a desired location on the maxilla or mandible. If the dental component is only a part of a complete dental fixture, the entire dental fixture (including dental component to be tested) is fastened in the desired location on the maxilla or mandible. For example, when testing a dental implant, the complete implant restoration is assembled and fastened in the desired location on the jaw. Similarly, in the case of testing a dental material, the material may be, for example, in the form of an artificial tooth or a filling to be applied to a tooth. In each case, the dental material under test would be associated with some form of fixture (i.e., an artificial tooth) which is fastened to the jaw.

Once the dental component or material under test is in place on jaw model 14, loading mechanism is adjusted up or down by turning hex flange 62 of loading member 50. This adjustment step causes the occlusal force on mandible 16 and maxilla 18 to be adjusted accordingly. Using strain gauge meter 110, the operator reads display 112 to determine when, during adjustment of mechanism 44, a desired occlusal force has been applied to mandible 16 and maxilla 18. Once the desired static occlusal force has been set, lock nut 63 on member 50 is tightened down on bushing 60 to lock member 50 in position. Mandible 16 is then moved relative to maxilla 18, such that the dental component or material under test is stressed during such movement. The test may require lateral movements (or excursions) of mandible 16, protrusive movements (or excursions) of mandible 16, or both lateral and protrusive movements (or excursions).

In order to effect lateral excursions of mandible 16, the operator would close switch 87 to power motor 72. To effect protrusive excursions of mandible 16, the operator would close switch 89 to power motor 90. Both motors 72 and 90 may be powered simultaneously to effect both lateral and protrusive excursions of mandible 16. As best understood from FIGS. 2 and 3, plunger 48, under the urging of compression spring 58, responds to the movement of mandible 16, and does not interfere with such movement. The force on mandible 16 and maxilla 18 is constantly sensed by load cell 68, throughout each cycle of motion (or each excursion) of mandible 16.

Figure 11:
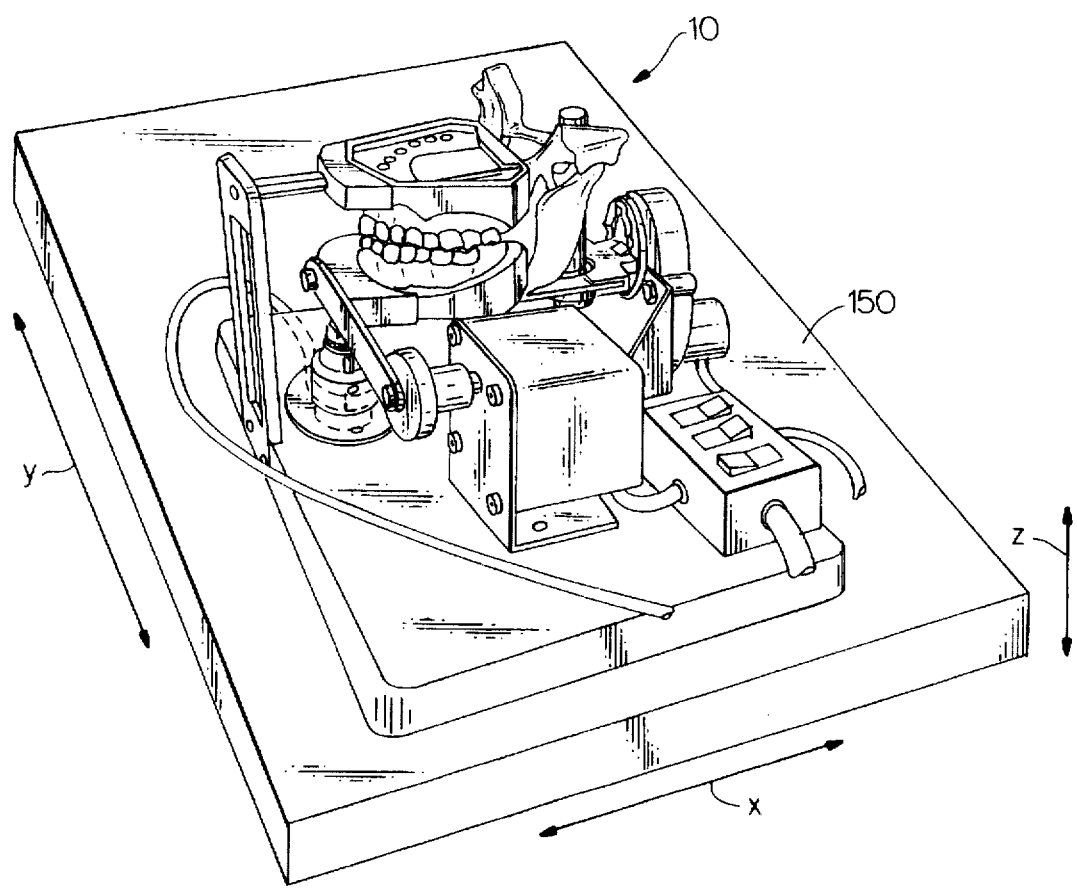
FIG. 11 is a perspective view of the dynamic jaw model apparatus of the present invention, mounted on a shake table.

The method of the present invention may further comprise the step of shaking jaw model 14, to introduce another source of stresses to the dental components or materials under test. As shown in FIG. 11, dynamic jaw model apparatus 10 is mounted on a shake table 150. Shake table 150 is a device which produces vibratory shaking movements in the directions indicated by arrows X, Y and Z. Shake tables are conventional and well known devices, and thus further description of same will not be necessary. The shaking motion of table 150 may be designed to simulate the conditions of the jaws while a human subject is walking, running, or traveling in some mode of transportation.

The testing method of the present invention may also include the step of measuring the forces sensed by load cell 68 and displaying the measurements with meter 110. Further, the method may include the step of storing and recording such measurements in processor 114.

While the above-mentioned method of the present invention has been described with respect to dental components or materials in general, apparatus 10 is particularly suited for testing dental implants. The specific method of implant testing includes the step of placing (or inserting) a dental implant in either mandible 16 or maxilla 18 of jaw model 14. As described above with reference to FIGS. 5–8, this step may involve the placement of more than one implant in both mandible 16 and maxilla 18. The next step of the method is to assemble a complete implant restoration at the desired jaw location (or locations), as described above with reference to FIG. 6–8. As in the general method, the next step is to apply an occlusal force to mandible 16 and maxilla 18, using loading mechanism 44. As in the general method, mandible 16 is moved laterally and/or protrusively relative to maxilla 18 in order to stress the dental implant. The occlusal force on the mandible and maxilla is sensed during the mandibular movements. Further, as with the general method, jaw model 14 may undergo a shaking step to add additional stresses to the implant(s) under test. Moreover, the forces sensed by load cell element 68 may be measured, displayed, and/or recorded as described above.

While the preferred embodiments of the invention have been particularly described in the specification and illustrated in the drawing, it should be understood that the invention is not so limited. Many modifications, equivalents, and adaptations of the invention will become apparent to those skilled in the art without departing from the spirit and scope of the invention as defined in the appended claims.

What I claim is:

1. An apparatus for modelling the physiological dynamics of a jaw, comprising:

a jaw model having a mandible and a maxilla;

loading means, coupled to said jaw model, for imposing an occlusal force on the mandible of said jaw model;

movement means, coupled to the mandible of said jaw model, for moving the mandible latreally relative to the maxilla; and sensor means for sensing occlusal forces on said jaw model during the lateral movement of mandible.

2. The apparatus as recited in claim 1, wherein said movement means includes means for moving the mandible protrusively relative to the maxilla.

3. The apparatus as recited in claim 1, further comprising meter means, coupled to said sensor means, for measuring the forces sensed by said sensor means.

4. The apparatus as recited in claim 3, wherein said meter means includes display means for displaying the forces measured by said meter means.

5. The apparatus as recited in claim 3, further comprising processor means, coupled to said meter means, for recording the forces measured by said meter means.

6. The apparatus as recited in claim 1, wherein said loading means includes resilient means, which engages the mandible of said jaw model, for urging the mandible against the maxilla of said jaw model to produce an occlusal force on said jaw model.

7. The apparatus as recited in claim 6, wherein said resilient means includes a hollow plunger in telescoping relation to a load member, and a compression spring seated inside the hollow plunger and the load member, the compression spring producing a direct force and a reactive force when the spring is compressed, the reactive force being proportional to the direct force, the direct force being transmitted to the plunger and the reactive force being transmitted to the load member, and wherein the plunger urges the mandible of said jaw model towards the maxilla of said jaw model with the direct force.

8. The apparatus as recited in claim 7, wherein said sensor means is a load cell operatively associated with the load member of said resilient means, such that the reactive force transmitted to the load member is sensed by the load cell.

9. The apparatus as recited in claim 8, wherein said resilient means includes adjustment means for adjusting the amount of the direct force applied to the mandible of said jaw model.

10. The apparatus as recited in claim 1, wherein the mandible and the maxilla of said jaw model each include a mounting plate to which dental fixtures may be secured.

11. The apparatus as recited in claim 10, further comprising a first plurality of dental fixtures secured to the mounting plate of the mandible and a second plurality of dental fixtures secured to the mounting plate of the maxilla.

12. The apparatus as recited in claim 11, wherein said first plurality of dental fixtures and said second plurality of dental fixtures are artificial teeth.

13. The apparatus as recited in claim 10, further comprising a threaded bushing secured into at least one of the mounting plates of the mandible or the maxilla of said jaw model, said threaded bushing being dimensioned to receive therein a threaded dental implant.

14. The apparatus as recited in claim 13, further comprising a dental implant threaded into said bushing.

15. The apparatus as recited in claim 14, further comprising an implant abutment having a screw portion threaded into said dental implant.

16. The apparatus as recited in claim 15, further comprising an artificial tooth being fastened to said implant abutment with a screw.

17. A method of testing a dental component or material, comprising the steps of:
   fastening to a jaw model a dental fixture with which the dental component or material under test is associated, the jaw model including a first jaw and a second jaw;
   applying an occlusal force on the jaw model;
   moving the first jaw laterally relative to the second jaw such that the dental component or material under test is stressed during the lateral movement; and
   sensing occlusal forces on the model jaw during the step of moving the first jaw laterally relative to the second jaw.

18. The method of testing as recited in claim 17, further comprising the step of shaking the jaw model.

19. The method of testing as recited in claim 17, further comprising the step of moving the first jaw protrusively relative to the second jaw; and wherein the sensing step occurs during both the lateral and protrusive movement steps.

20. The method of testing as recited in claim 17, further comprising the step of adjusting the amount of occlusal force applied to the jaw model.

21. The method of testing as recited in claim 17, further comprising the step of measuring the forces sensed during said sensing step.

22. The method of testing as recited in claim 21, further comprising the step of recording the forces measured during said measuring step.

23. The method of testing as recited in claim 21, further comprising the step of displaying the forces measured during said measuring step.

24. A method of testing a dental implant using a jaw model having a first dentulous artificial jaw and a second dentulous artificial jaw, said method comprising the steps of:
   placing the dental implant under test in either one of the first or the second artificial jaws of said jaw model;
   assembling a complete implant restoration, including artificial tooth, with the dental implant under test;
   applying an occlusal force on the jaw model;
   moving the first jaw laterally or protrusively relative to the second jaw such that said dental implant under test is stressed during said jaw movement; and
   sensing occlusal forces on the model jaw during the step of moving the first jaw relative to the second jaw.

25. The method of testing as recited in claim 24, further comprising the step of shaking the jaw model.

26. The method of testing as recited in claim 24, wherein said step of moving the first jaw relative to the second jaw includes moving the first jaw through lateral excursions.

27. The method of testing as recited in claim 24, wherein said step of moving the first jaw relative to the second jaw includes moving the first jaw through protrusive excursions.

28. The method of testing as recited in claim 24, further comprising the step of adjusting the amount of occlusal force applied to the jaw model.

29. The method of testing as recited in claim 24, further comprising the step of measuring the forces sensed during said sensing step.

30. The method of testing as recited in claim 29, further comprising the step of recording the forces measured during said measuring step.

31. The method of testing as recited in claim 29, further comprising the step of displaying the forces measured during said measuring step.

32. An apparatus for modelling the physiological dynamics of a jaw, comprising:
   a jaw model having a mandible and a maxilla;
   loading means, coupled to said jaw model, for imposing an occusal force on the mandible of said jaw model;
   movement means, coupled to the mandible of said jaw model, for moving the mandible protrusively relative to the maxilla; and
   sensor means for sensing occlusal forces on said jaw model during the protrusive movement of the mandible.

33. A method of testing a dental component or material, comprising the steps of:
   fastening to a jaw model a dental fixture with which the dental component or material under test is associated, the jaw model including a first jaw and a second jaw;
   applying an occusal force on the jaw model;
   moving the first jaw protrusively relative to the second jaw such that the dental component or material under test is stressed during the protrusive movement; and
   sensing the forces on the model jaw during the step of moving the first jaw protrusively relative to the second jaw.

* * * * *

UNITED STATES PATENT AND TRADEMARK OFFICE
CERTIFICATE OF CORRECTION

PATENT NO. : 5,743,732

DATED : April 28, 1998

INVENTOR(S) :
Jeffrey A. Watson

Page 1 of 2

It is certified that error appears in the above-indentified patent and that said Letters Patent is hereby corrected as shown below:

In col.10, line 13, "latreally" should read --laterally.--

In col. 12, line 2, "or protrusively" is deleted.

Claims 34 - 41 are inserted:

34. The method of testing as recited in claim 24, further comprising the step of moving the first jaw protrusively relative to the second jaw.

35. A method of testing a dental implant using a jaw model having a first dentulous artificial jaw and a second dentulous artificial jaw, said method comprising the steps of:
   placing the dental implant under test in either one of the first or the second artificial jaws of said jaw model;
   assembling a complete implant restoration, including artificial tooth, with the dental implant under test;
   applying an occlusal force on the jaw model;
   moving the first jaw protrusively relative to the second jaw such that said dental implant under test is stressed during said jaw movement; and
   sensing occlusal forces on the model jaw during the step of moving the first jaw relative to the second jaw.

36. The method of testing as recited in claim 35, further comprising the step of moving the first jaw laterally relative to the second jaw.

UNITED STATES PATENT AND TRADEMARK OFFICE
CERTIFICATE OF CORRECTION

PATENT NO. : 5,743,732
DATED : April 28, 1998
INVENTOR(S) : Jeffrey A. Watson

It is certified that error appears in the above-indentified patent and that said Letters Patent is hereby corrected as shown below:

37. The method of testing as recited in claim 35, further comprising the step of adjusting the amount of occlusal force applied to the jaw model.

38. The method of testing as recited in claim 35, further comprising the step of measuring the forces sensed during said sensing step.

39. The method of testing as recited in claim 35, further comprising the step of shaking the jaw model.

40. The method of testing as recited in claim 38, further comprising the step of recording the forces measured during said measuring step.

41. The method of testing as recited in claim 38, further comprising the step of displaying the forces measured during said measuring step.

Patent Claims 26 and 27 filed as claims 30 and 31 have been cancelled.

Signed and Sealed this

Third Day of November, 1998

*Attest:*

BRUCE LEHMAN

*Attesting Officer*   Commissioner of Patents and Trademarks